United States Patent [19]

Kusaba et al.

[11] Patent Number: 6,121,476

[45] Date of Patent: Sep. 19, 2000

[54] PROCESS FOR PREPARING DITHIOCARBONIMIDE DERIVATIVES

[75] Inventors: Tomoyuki Kusaba; Akiko Kakimizu; Kazuya Ujihara, all of Takarazuka, Japan

[73] Assignee: Sumitomo Chemical Company, Limited, Osaka, Japan

[21] Appl. No.: 08/864,371

[22] Filed: May 28, 1997

[30] Foreign Application Priority Data

May 28, 1996 [JP] Japan ..................................... 8-133182

[51] Int. Cl.⁷ ................................................. C07C 333/24
[52] U.S. Cl. .............................. 558/2; 546/115; 546/194; 549/462; 558/1
[58] Field of Search .................... 558/1, 2; 546/115, 546/194; 549/462

[56] References Cited

FOREIGN PATENT DOCUMENTS

| 0617014 | 9/1994 | European Pat. Off. . |
| 0656351 | 6/1995 | European Pat. Off. . |
| 4424788 | 6/1995 | Germany . |

*Primary Examiner*—Peter O'Sullivan
*Attorney, Agent, or Firm*—Sughrue, Mion, Zinn, Macpeak & Seas, PLLC

[57] ABSTRACT

The purpose of the invention is to provide a process for advantageous production of dithiocarbonimide derivatives of the formula I:

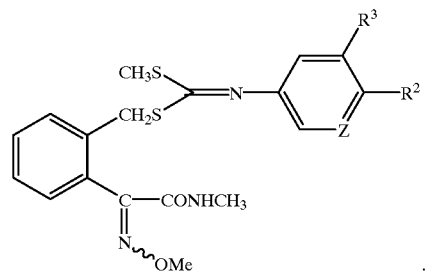

9 Claims, No Drawings

PROCESS FOR PREPARING DITHIOCARBONIMIDE DERIVATIVES

FIELD OF THE INVENTION

The present invention relates to a process for preparing a dithiocarbonimide derivative.

DESCRIPTION OF THE PRIOR ART

JP-A-8-73424 descloses that dithiocarbonimide derivatives represented by the formula I:

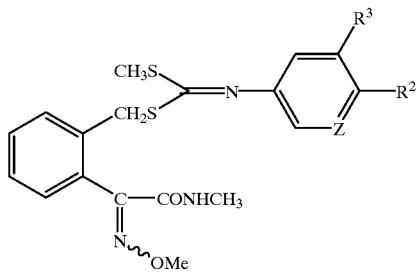

wherein $R^2$ and $R^3$ are the same or different and represent each a hydrogen atom, a C1–C6 alkyl group, a halogen atom, a C1–C6 alkoxy group, a C1–C6 haloalkyl group or a C1–C6 haloalkoxy group; or $R^2$ and $R^3$ together represent a methylenedioxy group which may be substituted by a fluorine atom; and Z represents a group: CH or a nitrogen atom, and the like have an excellent effect in combatting plant diseases and therefore there is a continuous demand on a process for advantageous production of said derivatives.

SUMMARY OF THE INVENTION

Under these conditions, the present inventors have conducted extensive studies seeking for a process for advantageous production of the dithiocarbonimide derivatives represented by the formula I and, as the result, they have discovered that the dithiocarbonimide derivatives represented by the formula I can readily be produced by reacting a keto-ester compound represented by the formula II with a dithiocarbamate compound represented by the formula III in the presence of a base to give a keto-ester derivative represented by the formula IV, then reacting said keto-ester derivative with methylamine to give a keto-amide derivative represented by the formula V, and then reacting said keto-amide derivative with O-methyl-hydroxylamine, and successfully completed the present invention.

Accordingly, the present invention provides a process for preparing the dithiocarbonimide derivative represented by the formula I, described above, which comprises reacting (hereinafter, referred to as Reaction 1) a keto-ester compound represented by the formula II:

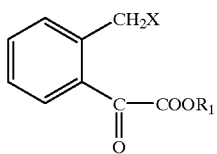

wherein $R^1$ represents a C1–C6 alkyl group and X represents a halogen atom,
with a dithiocarbamate compound represented by the formula III:

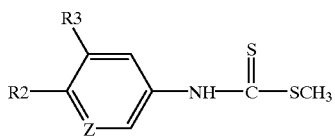

wherein $R^2$ and $R^3$ are the same or different and represent each a hydrogen atom, a C1–C6 alkyl group, a halogen atom, a C1–C6 alkoxy group, a C1–C6 haloalkyl group or a C1–C6 haloalkoxy group; or $R^2$ and $R^3$ together represent a methylenedioxy group which may be substituted by a fluorine atom; and Z represents a group: CH or a nitrogen atom, in the presence of a base to give a keto-ester derivative represented by the formula IV:

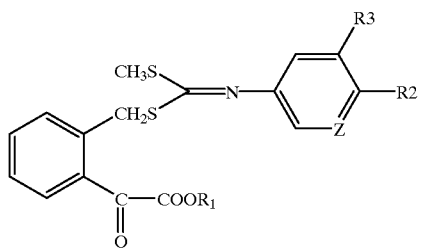

wherein $R^1$, $R^2$, $R^3$ and Z have the same meaning as defined above, then reacting (hereinafter, referred to as Reaction 2) said keto-ester derivative with methylamine to give a keto-amide derivative represented by the formula V:

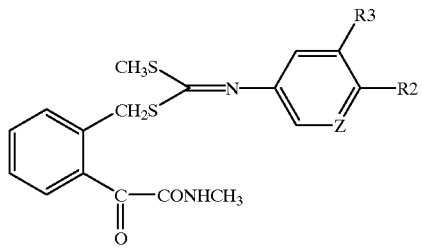

wherein $R^2$, $R^3$ and Z have the same meaning as defined above, and then reacting (hereinafter, referred to as Reaction 3) said keto-amide derivative with O-methyl-hydroxylamine.

Further, the present invention also provides the keto-ester derivative represented by the formula IV described above, and the keto-amide derivative represented by the formula V described above, which are useful as intermediates for producing the dithiocarbonimide represented by the formula I described above.

DESCRIPTION OF THE PREFERRED EMBODIMENT

In the present invention,
as the group represented by $R^1$, the C1–C6 alkyl group includes methyl group, ethyl group and the like;
as the group represented by $R^2$ and $R^3$, the C1–C6 alkyl group includes a methyl group, an ethyl group, an isopropyl group and the like;
the halogen atom includes fluorine atom, chlorine atom and the like;
the C1–C6 alkoxy group includes methoxy group, ethoxy group and the like;

the C1–C6 haloalkyl group includes trifluoromethyl group and the like;
the C1–C6 haloalkoxy group includes trifluoromethoxy group and the like.

as the group represented by X, the halogen atom includes chlorine atom, bromine atom and iodine atom.

In the present invention, a preferred example includes a methyl group, an ethyl group and an isopropyl group for $R^1$, a methyl group, an ethyl group and a trifluoromethyl group for $R^2$, a hydrogen atom for $R^3$ and the group: CH for Z.

A detailed description is given for Reaction 1.

The base usable herein includes, alkali metal alkoxides (for example, C1–C5 alkoxides such as tert-butoxide, methoxide, ethoxide, isopropoxide or the like), for example, tert-butoxide and the like; alkali metal hydrides, for example, sodium hydride and the like; alkali metal hydroxides, for example, sodium hydroxide, potassium hydroxide and the like.

The reaction is usually carried out in a solvent. Usable solvent varies depending on the base used and includes ethereal solvents, for example, tetrahydrofuran (hereinafter, abbreviated as THF), diethyl ether, dibutyl ether and the like; alcoholic solvents, for example, methanol, ethanol, isopropanol and the like; aromatic hydrocarbon solvents, for example, toluene, xylene, benzene and the like; halogenated aromatic hydrocarbon solvents, for example, chlorobenzene, dichlorobenzene and the like; aliphatic hydrocarbon solvents, for example, hexane, heptane and the like; N,N-dimethylformamide; water and so on or a mixed solvent thereof.

The reaction temperature is usually –10 to +60° C. and the reaction period is usually 0.5–10 hours. The ratio of the reactants and the base to be used in the reaction is usually in a range of from 1:0.8 to 08:1, or equimolar ratio or substantially equimolar ratio.

The reaction solution after completion of the reaction is usually treated with, for example, water, aqueous ammonium chloride or diluted hydrochloric acid and the organic phase is concentrated and subjected, if necessary, to purification such as chromatography or the like to isolate the desired keto-ester derivative represented by the formula IV.

Examples of the keto-ester derivative represented by the formula IV produced in such manner include:

N-(4-methylphenyl)-S-methyl-S-[2-(α-oxo-α-methoxycarbonyl)-methyl]phenylmethyl dithiocarbonimide, N-(4-ethylphenyl)-S-methyl-S-[2-(α-oxo-α-methoxycarbonyl)-methyl]phenylmethyl dithiocarbonimide, N-(4-trifluoromethylphenyl)-S-methyl-S-[2-(α-oxo-α-methoxycarbonyl)-methyl]phenylmethyl dithiocarbonimide, N-(4-methylphenyl)-S-methyl-S-[2-(α-oxo-α-ethoxycarbonyl)-methy]phenylmethyl dithiocarbonimide, N-(4-ethylphenyl)-S-methyl-S-[2-(α-oxo-α-ethoxycarbonyl)-methyl]phenylmethyl dithiocarbonimide, N-(4-trifluoromethylphenyl)-S-methyl-S-[2-(α-oxo-α-ethoxycarbonyl)-methyl]phenylmethyl dithiocarbonimide, N-(4-methylphenyl)-S-methyl-S-[2-(α-oxo-α-isopropoxycarbonyl)-methyl]phenylmethyl dithiocarbonimide, N-(4-ethylphenyl)-S-methyl-S-[2-(α-oxo-α-isopropoxycarbonyl)-methyl]phenylmethyl dithiocarbonimide, N-(4-trifluoromethylphenyl)-S-methyl-S-[2-(α-oxo-α-isopropoxycarbonyl)-methyl]phenylmethyl dithiocarbonimide, and the like.

The keto-ester compound represented by the formula II used in Reaction 1 includes, for example,
methyl 2-(bromomethyl)benzoylformate,
ethyl 2-(bromomethyl)benzoylformate,
isoprpyl 2-(bromomethyl)benzoylformate,
methyl 2-(chloromethyl)benzoylformate,
ethyl 2-(chloromethyl)benzoylformate,
isoprpyl 2-(chloromethyl)benzoylformate, and the like and these compounds can be prepared according to the following scheme:

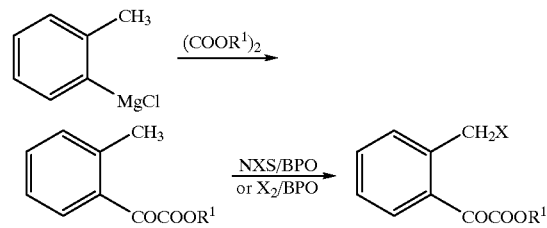

wherein NXS represents N-halogenosuccinimide such as N-bromosuccinimide, N-chlorosuccinimide, or N-iodogenoosuccinimide, BPO represents benzoyl peroxide and $R^1$ has the same meaning as defined above.

The dithiocarbamate compound represented by the formula III used in Reaction 1 includes, for example,
methyl 4-methylphenyl dithiocarbamate,
methyl 4-ethylphenyl dithiocarbamate,
methyl 4-trifluoromethylphenyl dithiocarbamate,
and the like and these compounds can be prepared according to the following scheme:

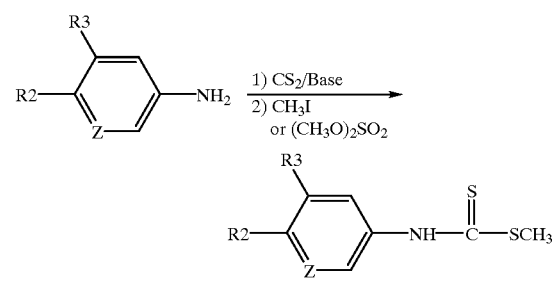

wherein $R^2$, $R^3$ and Z have the same meaning as defined above.

A detailed description is given for Reaction 2.

The reaction is usually carried out in a solvent. Usable solvent includes alcoholic solvents, for example, methanol, ethanol, isopropanol and the like; ethereal solvents, for example, THF, diethyl ether, dibutyl ether and the like; aromatic hydrocarbon solvents, for example, toluene, xylene, benzene and the like; halogenated aromatic hydrocarbon solvents, for example, chlorobenzene, dichlorobenzene and the like; aliphatic hydrocarbon solvents, for example, hexane, heptane and the like; N,N-dimethylformamide; water and so on or a mixed solvent thereof.

The reaction temperature is usually –10 to +60° C. and the reaction period is usually 0.5 to 10 hours. The ratio of the methylamine used in the reaction is usually 1 to 10 moles per mole of the keto-ester derivative of the formula IV.

The reaction solution after completion of the reaction is usually concentrated and subjected, if necessary, to purification such as recrystallization, chromatography or the like to isolate the desired keto-amide derivative represented by the formula V.

Examples of the keto-amide derivative represented by the formula V produced in such manner include:

N-(4-methylphenyl)-S-methyl-S-{2-[α-oxo-α-(N-methylcarbamoyl)]-methyl}phenylmethyl dithiocarbonimide, N-(4-ethylphenyl)-S-methyl-S-{2-[α-oxo-α-(N-methylcarbamoyl)]-methyl}phenylmethyl dithiocarbonimide, N-(4-trifluoromethylphenyl)-S-methyl-S-{2-[α-oxo-α-(N-methyl carbamoyl)]-methyl}phenylmethyl dithiocarbonimide, and the like.

A detailed description is given for Reaction 3.

In this reaction, O-methyl hydroxylamine or its organic or inorganic acid salt such O-methyl hydroxylamine hydrochloride, sulfate and the like can be used.

When O-methyl hydroxylamine acid salt is employed, 1 mole or more of a base is usually used in this reaction. The base to be used in this case includes an organic base as pyridine, sodium acetate or the like, or an inorganic base such as sodium carbonate, potassium carbonate, sodium hydrogencarbonate and the like.

The reaction is usually carried out in a solvent. Usable solvent includes pyridine; alcoholic solvents, for example, methanol, ethanol, isopropanol and the like; ethereal solvents, for example, THF, diethyl ether, dibutyl ether and the like; aromatic hydrocarbon solvents, for example, toluene, xylene, benzene and the like; halogenated aromatic hydrocarbon solvents, for example, chlorobenzene, dichlorobenzene and the like; aliphatic hydrocarbon solvents, for example, hexane, heptane and the like; N,N-dimethylformamide; water and so on or a mixed solvent thereof.

The reaction temperature is usually −10 to +60° C. and the reaction period is usually 0.5–10 hours. The ratio of the O-methylhydroxylamine used in the reaction is usually 1–2 moles per mole of the keto-amide derivative of the formula V.

The reaction solution after completion of the reaction is usually treated with, for example, water, aqueous ammonium chloride or diluted hydrochloric acid and the organic phase is concentrated and subjected, if necessary, to purification such as recrystallization, chromatography or the like to isolate the desired dithiocarbonimide derivative represented by the formula I.

Examples of the dithiocarbonimide derivative represented by the formula I produced in such manner include:

N-(4-methylphenyl)-S-methyl-S-{2-[α-methoxyimino-α-(N-methyl carbamoyl)]methyl}phenylmethyl dithiocarbonimide, N-(4-ethylphenyl)-S-methyl-S-{2-[α-methoxyimino-α-(N-methylc arbamoyl)]methyl}phenylmethyl dithiocarbonimide, N-(4-trifluoromethylphenyl)-S-methyl-S-{2-[α-methoxyimino-α-(N-methylcarbamoyl)]methyl}phenylmethyl dithiocarbonimide, and the like.

EXAMPLES

The present invention will now be described in more specifically by means of Preparation Examples and other Examples, which should not be construed as a limitation upon the scope of the present invention.

Preparation Example 1

(1) Methyl 4-ethylphenyldithiocarbamate (3.9 g) was added to a solution of ethyl 2-(bromomethyl)benzoylformate (5.0 g) in THF (50 ml). Under cooling with ice, potassium tert-butoxide (2.2 g) was added gradually to the solution. The mixture was stirred for 1 hour under cooling with ice and then heated at 50° C. for 1 hour. The reaction solution was cooled to room temperature and combined with water and ethyl acetate. Phases were separated and the organic phase was washed with water, dried over anhydrase magnesium sulfate and concentrated to give an oil. The oil was subjected to silica gel column chromatography (eluent: hexane/ethyl acetate=10/1) to give the desired N-(4-ethylphenyl)-S-methyl-S-[2-(α-oxo-α-ethoxycarbonyl)methyl]-phenylmethyl dithiocarbonimide (5.8 g, yield: 78%).

$^1$H-NMR (CDCl$_3$/TMS, 300 MHz, δ (ppm)): 1.23 (3H, t, J=8 Hz), 1.40 (3H, t, J=7 Hz), 2.43 (3H, s), 2.63 (2H, q, J=8 Hz), 4.42 (2H, q, J=7 Hz), 4.70 (2H, s), 6.76 (2H, d, J=8 Hz), 7.17 (2H, d, J=8 Hz), 7.3–7.8 (4H, m).

(2) To a solution of N-(4-ethylphenyl)-S-methyl-S-[2-(α-oxo-α-ethoxycarbonyl)methyl]phenylmethyl dithiocarbonimide (4.0 g)in methanol (20 ml) was added 40% methanolic methylamine solution (3.9 g) and the mixture was stirred at room temperature for 2 hours. The reaction solution was concentrated under reduced pressure to give an oil. The oil was subjected to silica gel column chromatography (eluent: hexane/ethyl acetate =2/1) to give the desired N-(4-ethylphenyl)-S-methyl-S-{2-[α-oxo-α-(N-methylcarbamoyl)]methyl}phenylmethyl dithiocarbonimide (3.3 g, yield: 87%).

$^1$H-NMR (CDCl$_3$/TMS, 300 MHz, δ (ppm)): 1.22 (3H, t, J=7.5 Hz), 2.40 (3H, s), 2.61 (2H, q, J=7.5 Hz), 2.87 (3H, d, J=5 Hz), 4.55 (2H, s), 6.74 (2H, d, J=8 Hz), 7.08 (1H, brs), 7.13 (2H, d, J=8 Hz), 7.3–8.0 (4H, m).

(3) To a solution of O-methylhydroxylamine hydrochloride (0.87 g) in pyridine (5 ml) was added N-(4-ethylphenyl)-S-methyl-S-{2-[α-oxo-α-(N-methylcarbamoyl)]methyl}phenylmethyl dithiocarbonimide (2.0 g) in one portion at room temperature and the mixture was stirred at room temperature for 2 hours. The reaction mixture was treated with 1N aqueous HCl until pH became acidic and shaken with ethyl acetate. Phases were separated and the organic phase was washed with aqueous sodium chloride, dried over anhydrous magnesium sulfate, concentrated under reduced pressure to give a yellow oil. The oil was subjected to silica gel column chromatography (eluent: hexane/ethyl acetate=2/1) to give the desired N-(4-ethylphenyl)-S-methyl-S-{2-[α-methoxyimino-α-(N-methylcarbamoyl)]methyl}phenylmethyl dithiocarbonimide (1.1 g, yield: 52%) as an approximately 9:4 mixture of E-form and Z-form.

$^1$H-NMR (CDCl$_3$/TMS, 300 MHz, δ (ppm))

E-form: 1.21 (3H, t, J=8 Hz), 2.42 (3H, s), 2.63 (2H, q, J=8 Hz), 2.84 (3H, d, J=6 Hz), 3.90 (3H, s), 4.18 (2H, s), 6.69 (2H, d, J=8 Hz), 7.13 (2H, d, J=8 Hz), 7.2–7.7 (5H, m).

Z-form: 1.21 (3H, t, J=7.5 Hz), 2.46 (3H, s), 2.60 (2H, q, J=7.5 Hz), 2.75 (3H, d, J=5 Hz), 4.01 (3H, s), 4.54 (2H, s), 6.73 (2H, d, J=8 Hz), 7.13 (2H, d, J=8 Hz), 7.2–7.7 (5H, m).

Further, by continuing elution with the above eluent, the starting compound N-(4-ethylphenyl)-S-methyl-S-{2-[α-oxo-α-(N-methylcarbamoyl)]-methyl}phenylmethyl dithiocarbonimide (0.9 g, 43%) was recovered.

Examples for producing the keto-ester compound represented by the formula II used in Reaction 1 are described below.

Reference Preparation Example 1

A solution of diethyl oxalate (30 g) in anhydrous THF (300 ml) was cooled to −30° C. A solution of o-tolyl magnesium chloride in THF (1 M, 140 ml) was added to the above solution at a temperature of the reaction solution of −20° C. After stirring at −30° C. for 30 minutes, the mixture was allowed to warm up to 0° C. and combined with an aqueous ammonium chloride solution. The mixture was concentrated under reduced pressure. The residue was treated with water and diethyl ether and phases were separated. The organic phase was washed with water, dried over anhydrous magnesium sulfate and concentrated to give a yellow oil. The oil was subjected to silica gel column chromatography (eluent: hexane/ethyl acetate=10/1) to give the desired ethyl 2-methylbenzoylformate (18 g, yield: 87%).

$^1$H-NMR (CDCl$_3$/TMS, 300 MHz, δ (ppm)): 1.42 (3H, t, J=6 Hz), 2.62 (3H, s), 4.45 (2H, q, J=6 Hz), 7.2–8.2 (4H, m).

To a solution of ethyl 2-methylbenzoylformate (10 g) in carbon tetrachloride (200 ml) were added N-bromosuccinimide (10 g) and 25%-hydrous benzoyl peroxide (1 g) and the mixture was heated under reflux for 2 hours. The reaction mixture was cooled with ice-water and filtered through a pad of Celite. The filtrate was concentrated under reduced pressure to give a yellow oil. The oil was subjected to silica gel column chromatography (eluent: hexane/ethyl acetate=20/1) to give the desired ethyl 2-(bromomethyl)benzoylformate (6.1 g, yield: 43%).

$^1$H-NMR (CDCl$_3$/TMS, 300 MHz, δ (ppm)): 1.42 (3H, t, J=6 Hz), 4.44 (2H, q, J=6 Hz), 4.88 (2H, s), 7.2–8.2 (4H, m).

Further, by continuing elution with the above eluent, the starting compound ethyl 2-methylbenzoylformate (4 g, 40%) was recovered.

Reference Preparation Example 2

To a solution of ethyl 2-methylbenzoylformate (10 g) in chlorobenzene (50 ml) were added a solution of bromine (10 g) in chlorobenzene (20 ml) and a suspension of 25%-hydrous benzoyl peroxide (1 g) in chlorobenzene (10 ml) over 2 hours and the mixture was heated under reflux for 1 hour. The reaction mixture was cooled with ice-water and filtered through a pad of celite. The filtrate was concentrated under reduced pressure to give a yellow oil. The oil was subjected to silica gel column chromatography (eluent: hexane/ethyl acetate=20/1) to give the desired ethyl 2-(bromomethyl)benzoylformate (1.4 g, yield: 10%).

Further, by continuing elution with the above eluent, the starting compound ethyl 2-methylbenzoylformate (6.3 g, 63%) was recovered.

An example for producing the dithiocarbamate compound represented by the formula used in Reaction 1 is described below.

To a solution of 4-ethylaniline (7.8 g) in diethyl ether (40 ml) were added carbon disulfide (6 g) and triethylamine (13 g). After stirring at room temperature for 2 hours, the precipitated crystals were collected by filtration and dried. The crystals (16 g) were dissolved in methanol (100 ml) and methyl iodide (7.6 g) was added dropwise thereto. The mixture was stirred at room temperature for 2 hours, acidified (pH =about 2) with in HCl and extracted with ethyl acetate. The organic phase was washed with water, dried over anhydrous magnesium sulfate and concentrated under reduced pressure to give a solid. The solid was treated with hexane, triturated, filtered and dried to give the desired methyl 4-ethylphenyldithiocarbamate (9.5 g, yield: 67%), m.p. 78° C.

What is claimed:

1. A process for preparing a dithiocarbonimide derivative represented by the formula I:

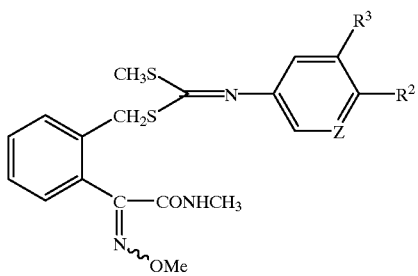

wherein R$^2$, R$^3$ and Z have the same meaning as defined below, which comprises reacting a keto-ester compound represented by the formula II:

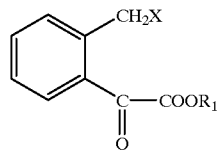

wherein R$^1$ represents a C1–C6 alkyl group, with a dithiocarbamate compound represented by the formula III:

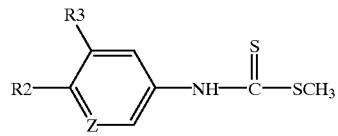

wherein R$^2$ and R$^3$ are the same or different and represent each a hydrogen atom, a C1–C6 alkyl group, a halogen atom, a C1–C6 alkoxy group, a C1–C6 haloalkyl group or a C1–C6 haloalkoxy group; or R$^2$ and R$^3$ together represent a methylenedioxy group which may be substituted by a fluorine atom; and Z represents a group: CH or a nitrogen atom, in the presence of a base to give a keto-ester derivative represented by the formula IV:

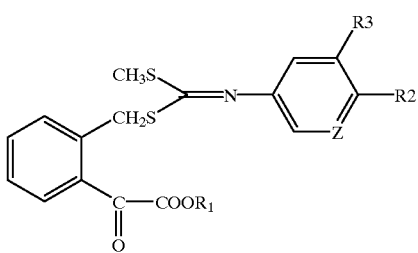

wherein R$^1$, R$^2$, R$^3$ and Z have the same meaning as defined above, then reacting said keto-ester derivative with methylamine to give a keto-amide derivative represented by the formula V:

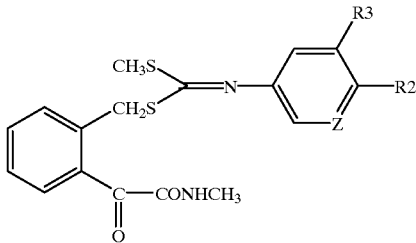

wherein $R^2$, $R^3$ and Z have the same meaning as defined above, and then reacting said keto-amide derivative with O-methyl-hydroxylamine.

2. The process according to claim 1, wherein $R^1$ is a methyl group or an ethyl group, $R^2$ is a methyl group, an ethyl group or a trifluoromethyl group, $R^3$ is a hydrogen atom and is a group: CH.

3. A keto-ester derivative represented by the formula IV:

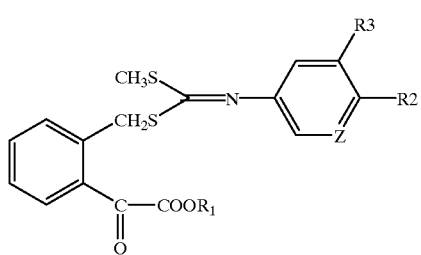

wherein $R^1$ is a C1–C6 alkyl group, $R^2$ and $R^3$ are the same or different and represent each a hydrogen atom, a C1–C6 alkyl group, a halogen atom, a C1–C6 alkoxy group, a C1–C6 haloalkyl group or a C1–C6 haloalkoxy group; or $R^2$ and $R^3$ together represent a methylenedioxy group which may be substituted by a fluorine atom; and Z represents a group: CH or a nitrogen atom.

4. The keto-ester derivative according to claim 3, wherein $R^1$ is a methyl group or an ethyl group, $R^2$ is a methyl group an ethyl group or a trifluoromethyl group, $R^3$ is a en atom and Z is a group: CH.

5. A keto-amide derivative represented by the formula V:

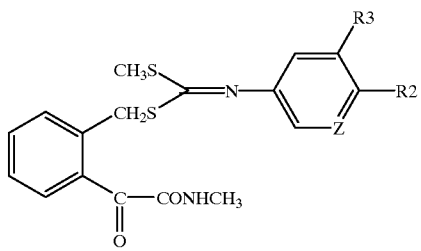

wherein $R^2$ and $R^3$ are the same or different and represent each a hydrogen atom, a C1–C6 alkyl group, a halogen atom, a C1–C6 alkoxy group, a C1–C6 haloalkyl group or a C1–C6 haloalkoxy group; or $R^2$ and $R^3$ together represent a methylenedioxy group which may be substituted by a fluorine atom; and Z represents a group: CH or a nitrogen atom.

6. The keto-amide derivative according to claim 5, wherein $R^2$ is a methyl group, an ethyl group or a trifluoromethyl group, $R^3$ is a hydrogen atom and Z is a group: CH.

7. A process for producing the keto-ester derivative of formula IV as defined in claim 3, which comprises reacting the keto-ester derivative of the formula II as defined in claim 1 with dithiocarbamate derivative of the formula III as defined claim 1 in the presence of a base.

8. A process for producing the keto-amide derivative of the formula V as defined in claim 5, which comprises reacting the the keto-ester derivative of the formula II as defined in claim 1 with a dithiocarbamate derivative of the formula III as defined in claim 1 in the presence of a base to give the keto-ester derivative of formula IV as defined in claim 3, and reacting the keto-ester derivative of formula IV obtained above with methylamine.

9. A process for producing the keto-amide derivative of the formula V as defined in claim 5, which comprises reacting the keto-ester derivative of formula IV as defined in claim 3 with methylamine.

* * * * *